United States Patent
Kyle et al.

(10) Patent No.: US 8,353,853 B1
(45) Date of Patent: Jan. 15, 2013

(54) ENCEPHALIC INSONICATION

(75) Inventors: Albert Kyle, Andover, MA (US);
Martin Mason, Andover, MA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 2148 days.

(21) Appl. No.: 10/350,764

(22) Filed: Jan. 24, 2003

(51) Int. Cl.
*A61B 8/00* (2006.01)

(52) U.S. Cl. .......................... 601/2; 600/459

(58) Field of Classification Search ........... 601/2–3; 600/439
See application file for complete search history.

(56) References Cited

U.S. PATENT DOCUMENTS

| | | | |
|---|---|---|---|
| 3,867,929 A * | 2/1975 | Joyner et al. | 601/166 |
| 5,501,655 A * | 3/1996 | Rolt et al. | 601/3 |
| 5,713,831 A | 2/1998 | Olson | |
| 5,752,515 A * | 5/1998 | Jolesz et al. | 600/458 |
| 6,296,619 B1 * | 10/2001 | Brisken et al. | 604/22 |
| 6,384,516 B1 * | 5/2002 | Fraser | 310/334 |
| 6,514,221 B2 * | 2/2003 | Hynynen et al. | 601/2 |
| 6,575,922 B1 * | 6/2003 | Fearnside et al. | 601/2 |
| 6,612,988 B2 * | 9/2003 | Maor et al. | 600/439 |
| 6,613,005 B1 * | 9/2003 | Friedman et al. | 601/2 |
| 6,635,017 B1 * | 10/2003 | Moehring et al. | 600/439 |
| 6,666,833 B1 * | 12/2003 | Friedman et al. | 601/2 |
| 6,682,502 B2 * | 1/2004 | Bond et al. | 604/22 |
| 6,733,450 B1 * | 5/2004 | Alexandrov et al. | 600/439 |
| 6,770,031 B2 * | 8/2004 | Hynynen et al. | 600/437 |
| 6,773,408 B1 * | 8/2004 | Acker et al. | 601/2 |
| 6,790,187 B2 * | 9/2004 | Thompson et al. | 601/2 |
| 7,037,267 B1 * | 5/2006 | Lipson et al. | 600/454 |
| 7,211,054 B1 * | 5/2007 | Francis et al. | 601/2 |
| 7,220,232 B2 * | 5/2007 | Suorsa et al. | 601/2 |
| 7,241,270 B2 * | 7/2007 | Horzewski et al. | 601/2 |
| 2001/0020127 A1 * | 9/2001 | Oshio et al. | 600/429 |
| 2002/0049395 A1 * | 4/2002 | Thompson et al. | 601/2 |
| 2002/0055693 A1 * | 5/2002 | Thompson et al. | 601/2 |
| 2002/0072690 A1 * | 6/2002 | Thompson et al. | 601/2 |
| 2002/0072691 A1 * | 6/2002 | Thompson et al. | 601/2 |
| 2002/0082529 A1 * | 6/2002 | Suorsa et al. | 601/2 |
| 2002/0091339 A1 * | 7/2002 | Horzewski et al. | 601/2 |
| 2002/0193708 A1 * | 12/2002 | Thompson et al. | 601/2 |
| 2004/0049134 A1 * | 3/2004 | Tosaya et al. | 601/2 |

OTHER PUBLICATIONS

Suchokova et al "Effect of 40-khz Ultrasound on Acute Thrombotic Ischemia in a Rabbit Femoral Artery Thrombosis Model" Circulation, May 16, 2000, 2296-2301.

* cited by examiner

*Primary Examiner* — Jonathan Cwern
(74) *Attorney, Agent, or Firm* — Vista IP Law Group LLP

(57) ABSTRACT

Apparatus for encephalic insonication, comprising a transducer array configured to safely insonicate a field in a human body of a size comparable to the spatial extent of the array itself. The array comprises a plurality of acoustic transducers arranged in a polygonal configuration and energized in subsets at frequencies between 200 and 400 kHz. A relatively uniform insonication of a field comparable in size to that of significant anatomical regions of the brain is obtained by driving the transducers in each subset in opposed phase relationship during at least part of the interval during which they are active. A pulsed driving scheme enables minimization of heating effects while providing significant therapeutic treatment. The apparatus is useful both with and without additional lytic agents.

57 Claims, 8 Drawing Sheets

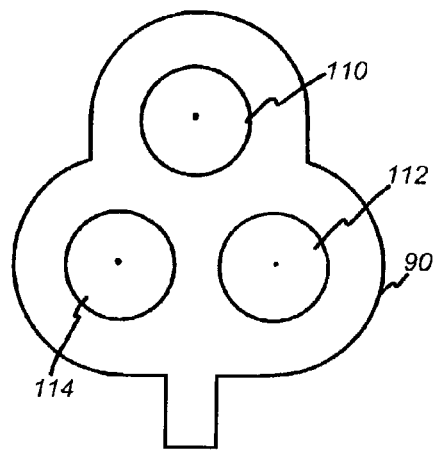
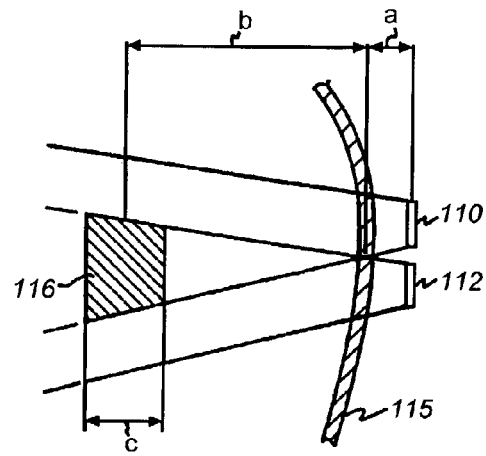
Fig. 7A  Fig. 7B
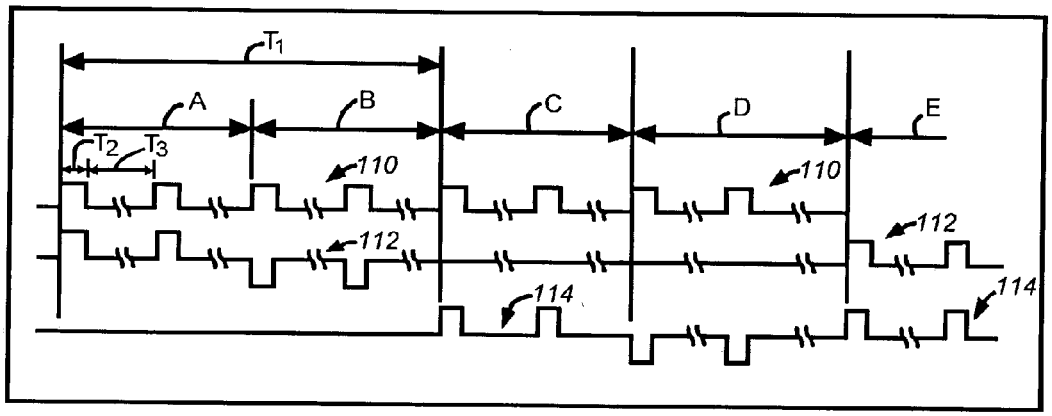
Fig. 8A
| 110 | 112 | 114 | |
|---|---|---|---|
| + | + |   | |
| + | − |   | |
| + |   | + | |
| + |   | − | 100a |
|   | + | + | |
|   | + | − | |
|   | OR |   | |
| + | + | + | |
| + | + | − | |
| + | − | + | 100b |
| − | + | + | |
Fig. 8B

ENCEPHALIC INSONICATION

BACKGROUND OF THE INVENTION

1. Field of the Invention

The invention relates to insonication of an animal body, and is particularly applicable to insonication of the human brain.

2. Background Information

Among the more significant causes of death or significant disability, stroke and ischemia of the brain are major factors. Stroke is commonly caused by the formation of thrombi, i.e., blood clots formed in the circulatory system of an animal body, including to the arteries, the veins, and the capillary system. When sufficiently large as to effectively occlude a vessel, they can cause heart attack or stroke, dependent on their location. When such thrombi form, it is essential to clear them in the shortest possible time, else death or at least significant damage may ensue. The time to treatment is critical for successful stroke therapy using thrombolytic agents. Only a small percentage (less than 20%) reach a hospital in time to qualify for such treatment.

Thrombolytic agents are frequently administered to break up or clear thrombi. It has been found in in-vitro and in animal studies that the action of such agents is often considerably enhanced by the application of ultrasound to the site in which a thrombus is located, concurrent with the injection of thrombolytic agents. The precise mechanism by which this occurs is still a matter of investigation but, regardless of the mechanism, the fact of improvement over a broad range of cases is well established.

The most common application of therapeutic ultrasound has been to the torso. Here, both external and catheter-delivery approaches have been used. Frequently, imaging procedures have first been used to locate a clot, and then therapeutic ultrasound is applied to reduce or eliminate the clot. The procedures are most commonly performed in hospitals, and by skilled medical personnel.

Blood clots in the brain have presented severe challenges to medical intervention. Because of the high risk associated with procedures affecting the brain, such procedures are typically left to the hands of highly skilled physicians called interventionalists. To the extent that ultrasound is used by such specialists, it is applied by way of intraarterial catheter. The procedure is difficult, time consuming, and carries significant risk, even when performed by highly skilled personnel. In a different but related disease, Vascular Cognitive Insufficiency (VCI), brain function is compromised by long term lack of blood flow. Thus, procedures which could temporarily or permanently increase blood flow to under-perfused regions of the brain would be of great value.

Similar considerations apply to treatment of ischemia. Recent studies in animal bodies have shown that ultrasound may enhance perfusion in ischemic tissue: see Siegel, J American College of Cardiology 1992; 20-732-5; Francis, Circulation 2000; 101:2296-2301. However, utilization of this approach for treatment of ischemia in the brain encounters all the obstacles faced when applying ultrasound to the brain for treatment of emboli.

Sonic therapy devices are most commonly employed in controlled environments such as hospitals, physician's offices, and the like, where size and transportability of the equipment are typically not major considerations, and where highly skilled personnel are generally available to operate the equipment. Such equipment is far less suited to environments such as ambulances and other emergency medical vehicles, where space is at a premium and where the personnel are commonly less intensively trained than those encountered in the typical hospital or private medical office setting.

Insonication of the brain presents unusual difficulties. The reasons are several. To begin with, unlike the torso, the skull is a significant barrier to the transmission of ultrasound energy through it. Thus, a large portion of the energy that is applied to the skull is consumed merely in heating the skull and raising its temperature at typical therapeutic frequencies. This limits the amount of energy that can be applied to dissolving the blood clot and can also cause patient discomfort and even injury if not carefully monitored.

Further, the precise location of an embolus of an area of inadequate perfusion within the body is frequently not known. Accordingly, it is necessary to provide the insonication over a large spatial extent. In the brain, for example, the volume to be treated may extend over a region on the order of 5 cm in diameter. Because of the uncertainty of the location of a thrombus in the region to be insonicated, it is desirable to provide a uniform intensity of insonication over the entire region, lest the specific site at which the thrombus is located receive too little energy or other sites too much. The need for coverage over an extended region, however, and that for uniform insonication over that region, present opposing considerations.

Specifically, the extent of field covered by a transducer varies inversely with the size of the transducer. Thus, a single large transducer will create a uniform field of only limited extent. Although arrays of transducers are known in other contexts (e.g., in application of ultrasound to the torso) in order to provide phased array scanning of a large area (see, for example, U.S. Pat. No. 6,384,516, issued May 7, 2002 to Fraser for "Hex Packed Ultrasonic Transducer Arrays") such scanning sweeps over a field a portion at a time, and does not irradiate an extended region uniformly. In addition, it requires many small elements and complex drive electronics to accomplish the scanning function. Similarly, U.S. Pat. No. 5,713,831, issued Feb. 3, 1998 to Olsson for "Method and Apparatus For Arterial Reperfusion Through Noninvasive Ultrasonic Action" proposes to use an array of transducers, each independently excited, to cover a larger area than that covered by a single transducer. Again, however, the field is effectively scanned, and the radiation is non-uniform.

SUMMARY OF THE INVENTION

In accordance with the present invention, we apply therapeutic ultrasound exteriorly of the skull of a patient in order to insonicate a field of substantial extent (i.e., of a size substantially larger than that provided by a single transducer and, specifically, on the order of 5 cm in diameter) and with a relatively uniform intensity distribution over the extent of the field (i.e., a power density variation of not greater than 6 dB over the field) During insonication, a relatively low intensity at the surface of the skull (e.g., preferably less than 2 Watts/$cm^2$) is maintained by distributing the energy at the skull surface over an area comparable to the area of the treatment zone. Because of the extended region over which insonication is efficiently obtained, the precise location of a clot need not be known in advance before effective ultrasound therapy can be undertaken.

The insonication is provided by means of a compact transducer array which is snugly fitted over the head of the patient. The array is mounted on a headpiece which specifically positions the array at a location which not only orients it for insonication of the region of the brain in which blood clots are most encountered (i.e., the circle of Willis and the mid-cerebral artery) but which also locates the array in a region of the skull at which a relatively high ultrasound transmission efficiency is obtained. It is preferably to positioned contralateral to (i.e., on the opposite side of) the side of the head from where the stroke is believed to have occurred. This not only locates the thrombus in the far field of the array, and thus provides a more nearly uniform insonication field, but also removes the heat generated by the array to a location more distant from the thrombus, a region which is often particularly sensitive to increased heat.

It is commonly believed that the greatest efficacy of insonication is at frequencies, well below the 200 kHz level, preferably at 20-30 kHz. However, we have found that such frequencies cannot effectively be used for encephalic insonication because they can be "heard" by a patient undergoing insonication, even though such frequencies are well beyond the normally audible range. The mechanism by which this occurs is believed to arise from ultrasonic conduction in the bone, which is then interpreted by the cochlea as audible sound. See Lenhardt, *Science,* 1991; 253, 282-285. The result can be painful for the patient, and discourages use of the treatment.

Additionally, ultrasound attenuation passing through the skull places an effective upper limit on the frequency, since the attenuation coefficient in dB increases as approximately $(f)^{1.2}$, where f is frequency. At 300 kHz the attenuation passing through the skull is ~8 dB. Thus about 16% of the energy passes through. Although this attenuation is high, it nonetheless allows sufficient energy transfer to reach therapeutic acoustic levels over the necessary brain regions. However, at 500 kHz the attenuation has increased to 13 dB, resulting in energy transmission of only 5%. This produces inadequate therapy levels, and would force one to constrain the energy to a more tightly focused beam, thus defeating the concept of regional treatment.

We have found that for therapeutic ultrasound delivery through the skull, an operating frequency from approximately 200 to 400 kHz is effective. This frequency range is sufficiently high that it is not "heard" by the patient, yet is still within a range that allows sufficient energy to pass through the skull and into the treatment region to provide meaningful therapeutic effect. In the preferred embodiment, we drive the transducer array at a frequency of approximately 300 k Hz.

The compact array of the present invention is formed preferably by two or more transducers arrayed in close proximity, such that the individual fields from the transducers substantially or completely overlap in the region to be treated. By overlapping the fields, the pressure created at a given point in the field is the phased sum of the individual contributions from each element. Two, three, four or more transducers may be used to form the array, with two or more transducers being driven simultaneously. and with differing phase between at least some of the active devices. This differs from a conventional phased array since the individual element size is much larger than that in a typical phased array, and the beam is not focused or steered. Rather, the multiple spatially and temporally overlapping beams are used to produce a large and relatively uniform field from an effectively large radiating surface. In the simplest approach, pairs of transducers are driven alternately in-phase and in opposed polarity.

Further, the transducers are sized and configured such that they provide little or no beam overlap at the skull, but substantial or complete beam overlap in the region to be treated. As a result, the beam intensity is controlled to acceptable limits at the skull surface (e.g., no more than 2 watts/cm$^2$ and preferably more nearly on the order of 1 watt/cm$^2$) while yet providing substantial intensity in the region to be treated but within safe insonication limits (e.g., a mechanical index of no greater than 0.5, preferably on the order of 0.3).

In one embodiment of the invention, we have used three transducers, arranged in a triangular configuration. The transducers each have an active diameter of 24 mm, and are spaced apart by 28 mm (center to center). They are driven at a nominal frequency of 300 kHz. Each transducer delivers an average acoustic power at the skin surface of approximately 1 watt, resulting in a mechanical index of 0.3 over a treatment region on the order of about 5 cm diameter at a depth of 8 cm into the skull. (The mechanical index is simply the power divided by the square root of the frequency, $P/f^{1/2}$, and is a common measure of the safety of insonication levels). With this arrangement, even though the individual transducers have a −3 db beamwidth of approximately 1.2 cm, the overall effective beamwidth (−3 db) of the array over the treatment region is approximately 5 cm in diameter. This is sufficient to cover the region of the brain where most ischemic strokes occur. To achieve a comparable size field with a single circular transducer, would require a transducer having a diameter of approximately 13 mm. The active radiating surface area of such a transducer would be nearly 7 times smaller, and the necessary surface intensity would be nearly 14 times higher, thus producing unacceptable pressures and heating.

In one embodiment of the invention, using an array of three transducers, the transducers are driven in pairs, the pairs being cyclically changed over the course of a treatment period, which last on the order of 60 minutes. During the treatment period, each pair of transducers is driven for an interval ("the active period") that is substantially less than the treatment period. For example, the active period during which a given transducer pair is selected for energization may be on the order of from 1 to 10 seconds duration.

As a further aspect of the invention, we have found that, when used in conjunction with a lytic agent, e.g., t-PA, the energy applied during the initial portion of an active period is more effective in producing lysis than energy delivered later in the active period. Thus, in the present invention, during a given active period, we do not drive the transducers continuously, but repeatedly cycle them "on" and "off" in pairs. In this manner, we have been able to obtain the desired lytic effect of the transducer energy while minimizing the "on" time of the transducers and thus of the power that they generate. This not only reduces the overall energy that must be absorbed by a patient during treatment, but also minimizes local heating and thus further enhances patient comfort and safety. In the preferred embodiment described herein, we use a cycle time on the order of 8 milliseconds. Within each cycle, the transducers are energized for only a portion of the cycle. In the particular embodiment described herein, they are energized for a time on the order of 5% of the cycle time, i.e., approximately 0.4 milliseconds. Further in accordance with the present invention, the transducers are preferably energized in-phase for a portion of the cycle time and are energized out-of-phase for the remaining portion. Preferably, these portions are of equal duration. Due to interference between the two transducer beams, the field created by the two beams covers the desired area but will have spatial peaks and nulls. By driving the transducers alternately in and out of phase, the positions of the peaks and nulls are changed or even reversed, resulting in a time average insonification that is more nearly uniform than that of the individual fields. A further increase in uniformity of insonication of a region of the brain can be achieved by varying the driving frequency of the input to the transducers by a small amount (Preferably less than approximately 10 kHz) during their active periods. The variation may be made continuously through the driving period, or may be made in small discrete steps. This effectively slowly sweeps the residual nulls and peaks of the radiation created by any reverberant standing waves across the brain, and thus helps to provide a more nearly uniform distribution of energy in the region being insonicated.

The apparatus of the present invention is used for treating thrombi in the brain, either in conjunction with the administration of a thrombolytic agent such as tPA or the like, or without such an agent. As with all blood clots, but particularly those in the brain, it is frequently of critical importance that therapy be administered within a short time of the formation of the clot, e.g., within minutes, as opposed to hours or days. However, before such therapy can be administered, it is generally considered necessary to perform a preliminary screening on the patient to insure that the patient is not suffering from a condition (e.g., internal cerebral bleeding) that would rule out the use of lytic agents. Thus, it is critical that a patient suffering a stroke be taken as quickly as possible to a medical facility which can perform the requisite screening; during transit to such a facility, the stroke is necessarily left untreated.

Recent studies have indicated that ultrasound, particularly low frequency ultrasound, may enhance perfusion in ischemic tissue surrounding a blood clot. See Suchkova et al., "Effect of 40-kHz Ultrasound on Acute Thrombotic Ischemia in a Rabbit Femoral Artery Thrombosis Model", Circulation, May 16, 2000, 2296-2301. However, such techniques have not heretofore been applied to treatment of ischemic diseases of the brain. We have determined, however, that ultrasound of the characteristics described herein and applied to the skull as set forth in detail below provides a meaningful beneficial increase in blood flow to under-perfused areas by stimulating vasodilation and enhancing collateral circulation. In particular, we have determined that the method and apparatus of the present invention are of significant benefit in treating acute ischemia, such as stroke, or a chronic ischemia, such as VCI, and can provide desirable, and possibly life-saving, therapy even prior to arrival of the patient at a medical facility. In particular, the transducer array is carried by a headpiece that is quickly, easily and accurately fitted to a patient by paramedics and other emergency medical personnel outside the usual medical facilities to and under field conditions, e.g., at the locus of a patient's stroke, in an ambulance, or the like. The headpiece carries a positioner element that correctly positions the array in relation to the temporal bone of the patient's skull to ensure optimal transmission of the ultrasound energy through the skull into the region to be treated. Thus, even during transit to a medical facility, the patient can thereby begin treatment to alleviate the effects of the is stroke.

BRIEF DESCRIPTION OF THE DRAWINGS

The invention description below refers to the accompanying drawings, of which:

FIG. 7A is a planar view of the transducer array used in the present invention;

FIG. 7B shows the insonication pattern and field provided by the transducer arrangement of FIG. 7A;

FIG. 8A is a plot showing timing relationships for activation of the transducer array;

FIG. 8B is a table showing exemplary energization sequences for the transducers to in the array.

DETAILED DESCRIPTION OF AN ILLUSTRATIVE EMBODIMENT

Figure 1A:
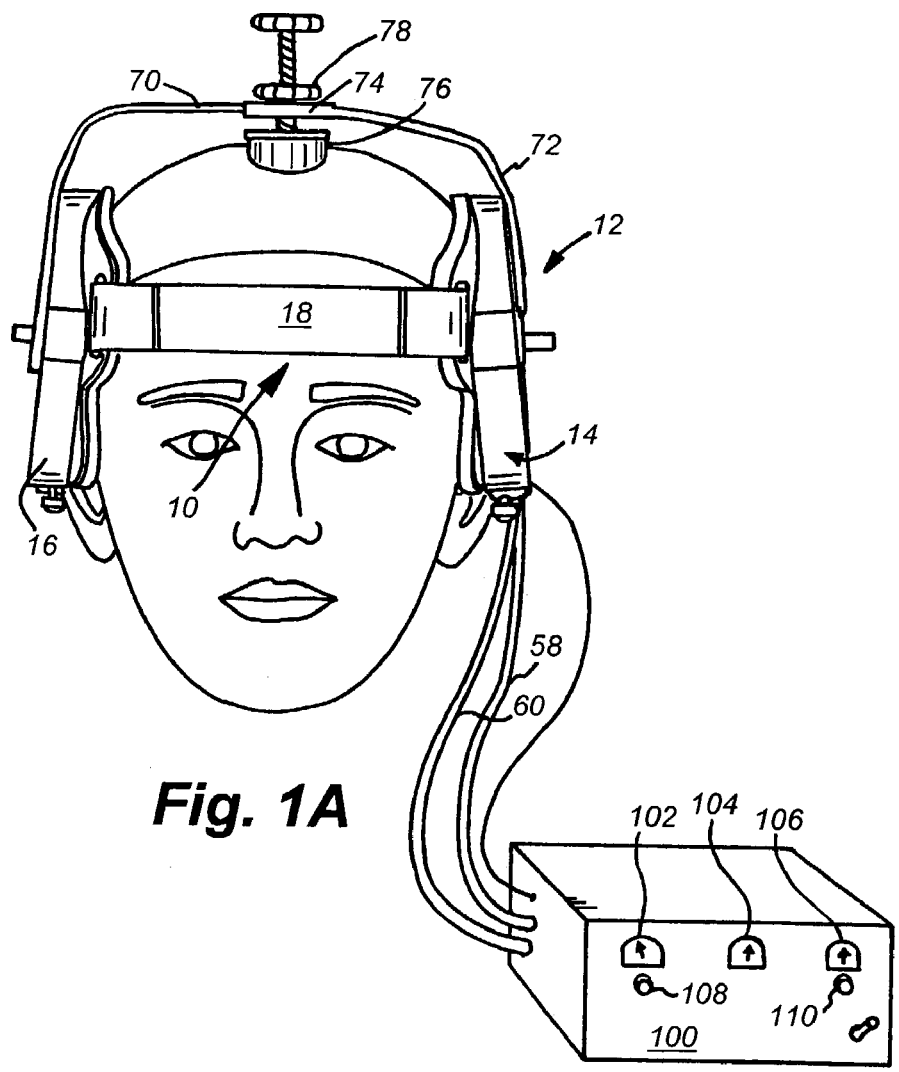
FIGS. 1A and 1B are front and side views, respectively, of a headpiece structured to precisely mount a transducer array in accordance with the present invention.
Figure 1B:
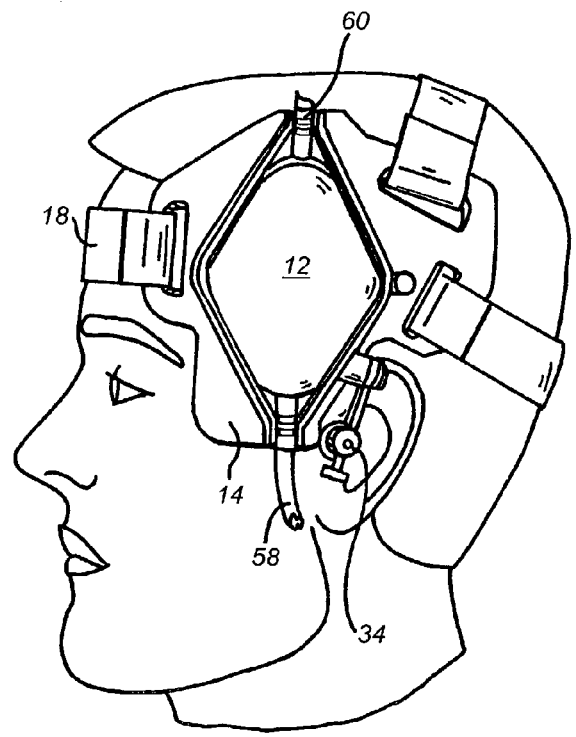
Figure 2:
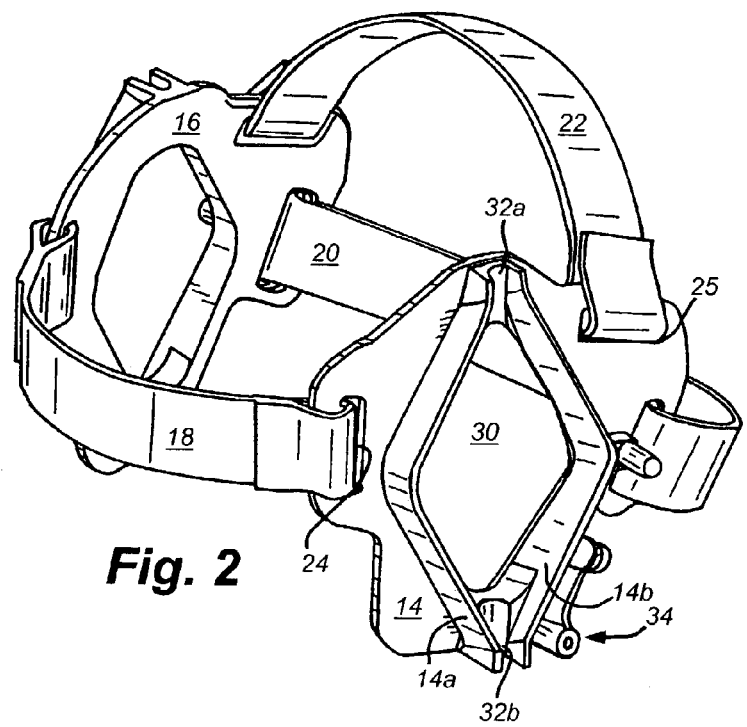
FIG. 2 is a view in perspective showing the headpiece of FIG. 1 in greater detail.

The following description of the invention will be best understood by concurrent examination of FIGS. 1A and 1B, which are front and side pictorial views of the apparatus of the present invention mounted on the head of a patient for treatment of an embolus in the brain, in conjunction with FIG. 2 which is a view in perspective of only a portion of the headpiece. In FIG. 1, the apparatus of the present invention comprises a head unit having an inner headpiece 10 and an outer driving unit 12. The headpiece 10 comprises a frame 14 connected to lateral and transverse flexible straps 18, 20, respectively. The length of each strap is adjustable to accommodate heads of various sizes. To this end, in the specific embodiment described herein, the opposite end of each strap has a fastening element (e.g., a strip of an interlocking material such as Velcro® fastener material) on opposed faces thereof to enable a technician to quickly slip the strap through a slot such as slots 24 or 25 on frame 14 and close it on itself to thereby secure the strap at a fixed length. Alternative means for adjusting the strap are well known and may be used.

The assembly depicted herein is specifically adapted for use on the left side of the skull. For use on the right side of the skull, the drive unit 10 is reversed so as to mount on the right side. Since they are otherwise the same, only frame 14 will be further described in detail. Frame 14 has a centrally formed aperture 30 defined by side walls 14a, 14b, respectively. The frame also has tubular grooves 32a and 32b formed therein, and has connected thereto a positioning structure 34 to accurately locate the headpiece at a position where the ultrasound energy most readily passes through the skull and from which the region in which brain thrombi most frequently form can readily be insonicated.

Figure 3A:
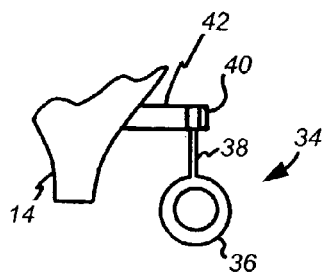
FIG. 3A is a sketch illustrating the manner in which the transducer array is precisely physiologically oriented on the patient's skull.
Figure 3B:
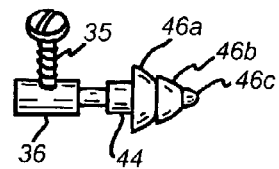
FIG. 3B is a side view of the locator arm of FIG. 3A.
Figure 3C:
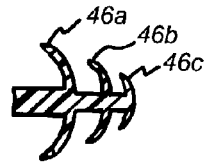
FIG. 3C is a side sectional view of the locator arm showing the flexible anchoring elements in detail.

FIGS. 3A and 3B are front and side elevational views showing the positioning structure 34 in more detail. The structure comprises a tubular shaft 36 connected to an arm 38 having an aperture 38a at its upper end; a screw 40 extends through the aperture to a post 42 extending from the frame 14. When the screw is tightened, it frictionally engages the arm 38 between itself and the post so that the arm can be rotated about the post and then frictionally held in a desired angular position. A removable insert 44 carries a series of flexible hemispherical shells 46a, 46b, 46c of resilient plastic material of the like and of increasingly diminished diameter spaced along the shaft thereof.

The structure 34 facilitates positioning the headpiece on a patient such that, when mounted on the headpiece, a transducer array is positioned over the temporal bone of the skull at a location maximally conducive to insonication of the skull.

In particular, in fitting the headpiece to a patient, the person attending the patient adjusts the headpiece until the positioning structure 34 can be into alignment with the patient's ear canal (meatus). He or she then presses insert 44, and thus shells 46, gently into the patient's ear canal in order to secure it in position, and then tightens the headpiece to the skull. This thereby fixes the alignment of the frames 12 with respect to the temporal area of the skull, and thus of the acoustic transducers which will be mounted on them, and thus provides positive anatomic positioning of the frame with respect to the temporal lobe of the patient's skull. This location allows efficient energy penetration of the skull for insonication of the circle of Willis and the mid-cerebral artery within the brain.

Figure 4A:
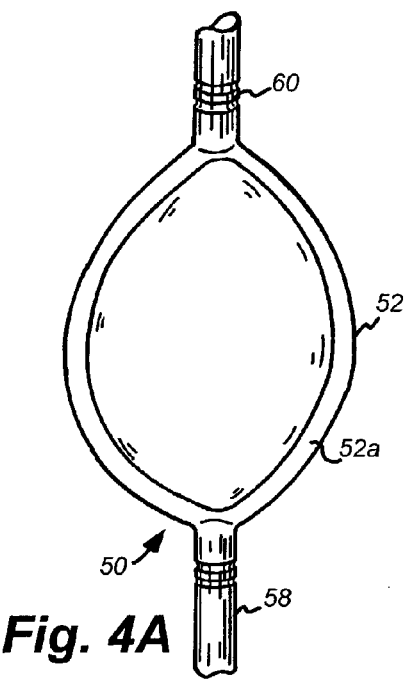
FIG. 4A is a top planar view of an interface element used in connection with the transducer array.
Figure 4B:
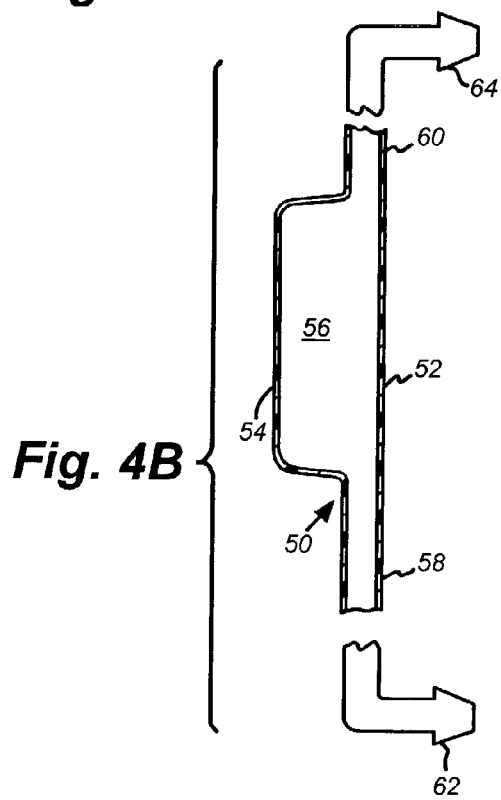
FIG. 4B is a side sectional view of the interface element taken along the lines 4B-4B of FIG. 4A.

A coolant pouch of a shape generally conformable to the aperture 30 is provided for use in connection with the headpiece 10. Such a pouch is shown in detail in FIGS. 4A and 4B. The pouch 50 is of a generally triangular shape and has a generally planar rear wall 52 to which is sealed a frontal wall 54 spaced from the rear wall to thereby form an interior cavity 56 between the two walls. Tubing 58, 60 extends into the cavity and carries fluid to and from the cavity. The tubing terminates in connectors 62, 64 which enable rapid engagement and disengagement with a fluid source. The pouches are desirably formed from a flexible, water-resistant material of plastic or the like.

Figure 5:
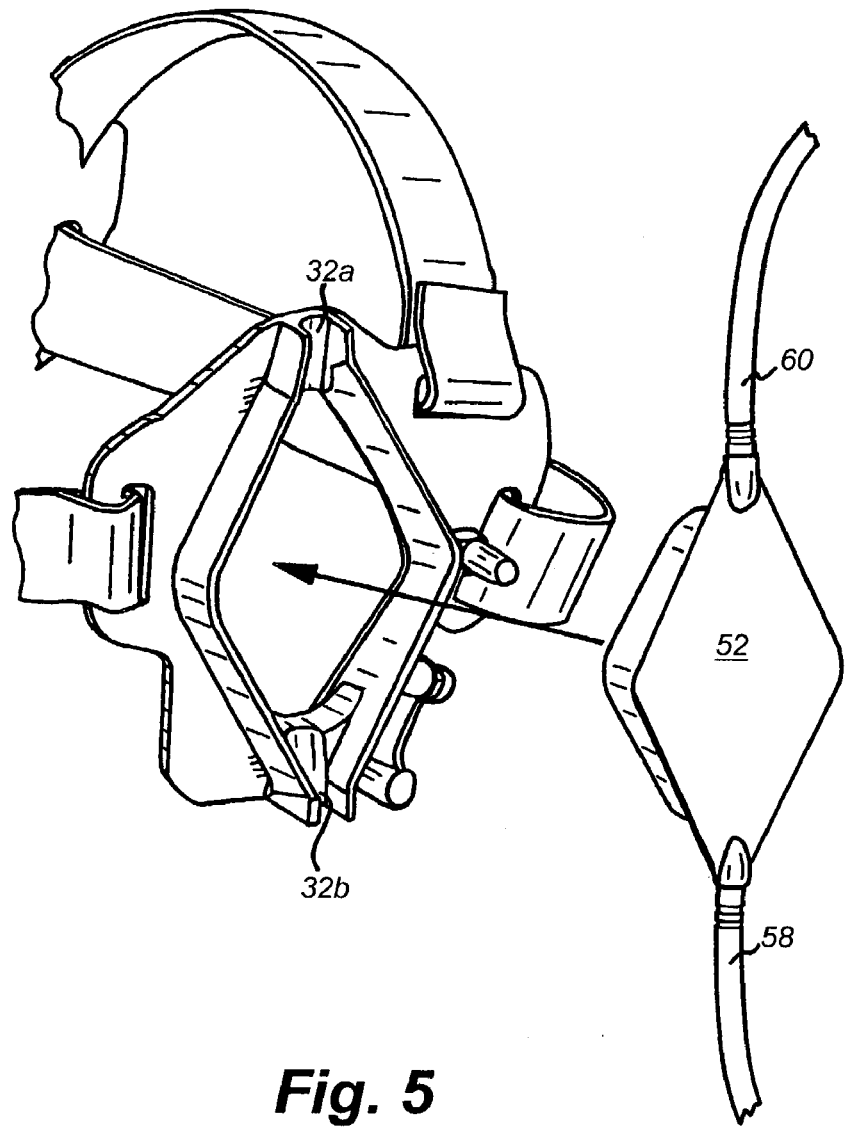
FIG. 5 is a sketch showing the interface element mounted to the headpiece of FIGS. 1 and 2.
Figure 6:
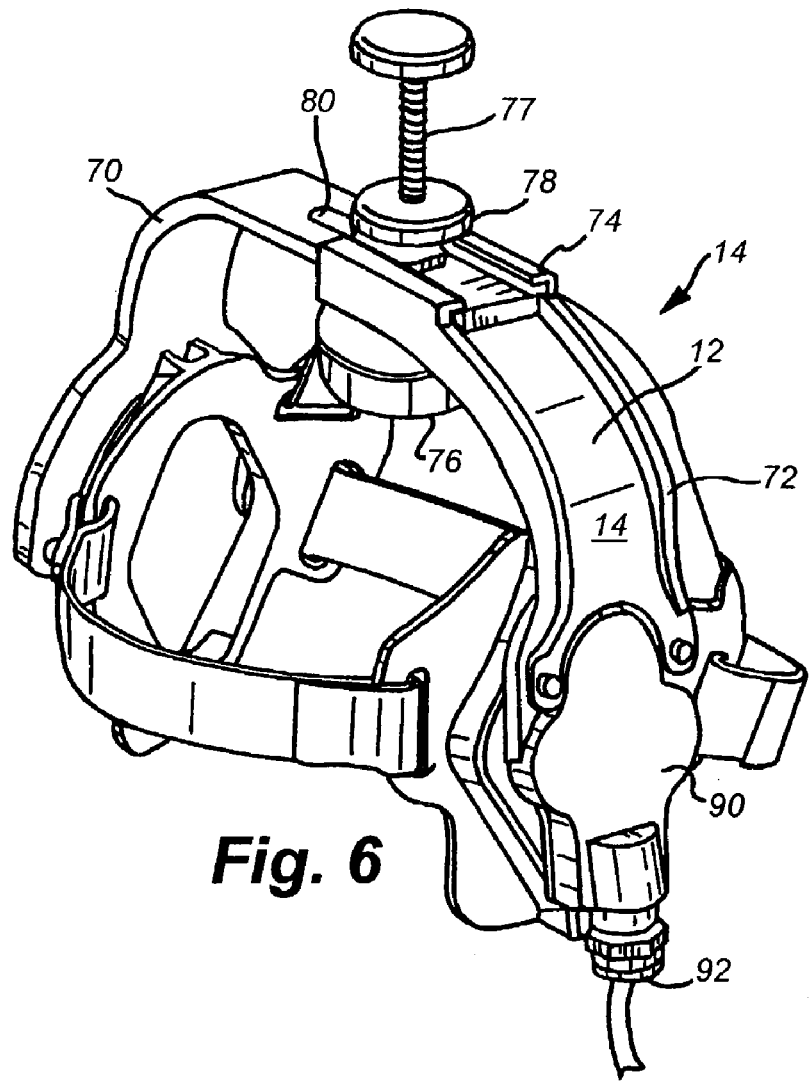
FIG. 6 is a view in perspective showing the transducer mount in more detail.

FIG. 5 shows the manner in which the pouches are mounted on the headpiece 10. In particular, a pouch 50 is fitted into the aperture 30 of receptor 14, the tubular lines 60 and 62 then being fitted into grooves 32a and 32b. A similar pouch (not shown) may be fitted into the aperture of frame 16. When coolant (typically water) flows through them, the pouches preferably assume a somewhat convex shape in order to snugly fit to the skull when the transducers are fitted over the pouch as shown in FIG. 6. During use, the pressure of the coolant flowing thorough them is preferably adjusted in order to control and limit the pressure applied by the pouch to the skull of the patient. The pouches not only provide cooling for the patient's skull, but also provide effective acoustic coupling between the transducers and the skull. Like the headpiece and the frames, they are readily manufacturable at low cost, and are thus disposable. It will be understood that alternative means of cooling the transducers may be used. For example, an active cooling element such as a thermo-electric cooling modules may be incorporated into, or associated with, the transducer housing in order to maintain the temperature of the transducers at an acceptable level.

Referring now to FIGS. 1A and 6, outer driving unit 12 is formed from shape-retaining left and right arches 70, 72, respectively. Arch 72 has a connector 74 into which arch 70 slides. A cushioning pad 76 is held on the shaft of a bolt 77 which extends through an aperture 80 of arch 70. A nut 78 moves along bolt 77 and adjusts the height of the cushion 76 with respect to a patient's head. Mounted on a remote end of the arch 72 is a transducer array housing 90.

When a patient is to be treated, the inner headpiece 10 is first placed on the patient's head, the straps 18, 20, 22 being only roughly adjusted to position the frame or frames 14, 16 over the patient's temple. One or both of the positioning structures 34 is then gently guided into the patient's ear canal, the cushion 76 being adjusted as necessary to facilitate this. This locates and orients the frame or frames 14, 16 at the correct position on the temple. and the straps 18, 20, 22 are then tightened as necessary to secure the headpiece to the patient's skull. Next, a pouch 50 is fitted into one of the frames 14, 16. The tubular connectors 62, 64 of the pouch are then connected into a control and monitoring unit 100 which circulates water or other coolant through the pouch when in operating mode. The outer driving unit 12 is then positioned over the inner headpiece 10 such that the transducer array housing is aligned with the flat rear face 52 of pouch 50. With this arrangement, the transducer array is located on the order of half an inch from the skull. Electrical leads 92 from this array are then plugged into the control and monitoring unit 100 in order to provide driving power for the transducer array. Indicators 102, 104 and 106 allow monitoring of the flow rate of coolant; the temperature at the patient's skull in the area in which sonic energy is being applied; and the power that is being applied. Controls 108 and 110 allow the operator to adjust the flow rate (and thus control the temperature) and the power level respectively.

FIG. 7A is a planar view of the transducer array within housing 90. The array comprises ultrasonic transducers 110, 112, 114 arranged in a triangular configuration. The transducers are driven at a frequency between 200 kHz and 400 kHz, preferably at about 300 kHz, and are driven in pairs, preferably alternating such that transducers 110 and 112 are driven during one sequence, then another pair such as transducers 110, 114, and then a third pair such as transducers 112, 114, before the cycle again repeats. Alternatively, all three transducers are driven simultaneously.

It is important to deliver adequate power to the site to be treated, while limiting the temperature rise of the body portion adjacent the transducers. In the present invention, this is achieved by structuring the transducers as described herein, as well as by controlling the driving structure of the signals applied to the transducers. FIG. 7B diagrammatically-depicts the insonication pattern and field provided by the transducer arrangement of FIG. 7A. Pairs of transducers, e.g. transducers 110 and 112, generate beams 110', 112', respectively, which diverge from these transducers. These edges of the beams represent the spatial extent over which the beam intensity is at or above a certain level, here, illustratively, at or above the −6 db power level. By virtue of the positioning of these beams, and the frequency at which they are driven, there is very little overlap of the beams at the surface of the skull 115, but increasing overlap within the skull (to the left of the skull portion 115). Within the treatment region 116, the overlap is substantial. It is this overlap that allows the positive interference effects which in turn produce a uniform insonication.

In the preferred embodiment described herein, with transducers of diameter 24 millimeters, spaced 26 millimeters apart, center to center, spaced from the skull by a "standoff" distance "a" of approximately 0.5 inch and driven at 300 kHz, the treatment to region is centered at a volume located at a distance "b" of approximately 2.5 inches into the skull and extends over a diameter "c" on the order of approximately 2 inches. It will be understood that one or more of these parameters may be varied to accommodate particular circumstances and requirements. For example, it is contemplated that the stand-off" distance "a" may vary from 0.5 inch to 2" in differing implementations, and the driving frequency may vary from 200 kHz to 400 kHz, among other possibilities Thus, by changing one or more of the transducer size, spacing, driving frequency and standoff distance from the skull, the treatment region may generally be positioned where desired, and significant energy may be delivered to the treatment region, while minimizing the energy delivered to, and dissipated in, the skull.

As noted above, the particular transducer driving pattern also contributes to the efficacy of the insonication. Thus, FIG. 8A shows one example of a transducer driving sequence for the transducers 110, 112, 114. As shown, each pair of transducers forming an active subset of the array is driven for a period $T_1$ ("the cycle period") that is desirably on the order of from one to ten seconds, preferably about six seconds, before the next transducer pair is activated. Further, within each such period, the driving signal is not applied continuously but is alternately turned "on" and "off" for finite intervals of time. Thus, as shown in FIG. 8A, the driving signal is "on" for an energization interval $T_2$ and "off" for a rest interval $T_3$. The optimal duty cycle (i.e., the "on" time of a pulse as a fraction of its total "on" and "off" time) and pulse repetition rate will, of course, vary as a function of the driving power level, transducer impedance, and skull impedance, among other factors. Examples of ranges of these variables are $T_2=0.0001$ to 1 second and $T_3=0.001$ to 4 seconds, corresponding to pulse repetition frequencies on the order of from less than 1 Hz to approximately 1 kHz. However, we have found surprisingly effective results when a pulse repetition rate on the order of about 125 Hz (i.e., $T_2+T_3=8$ ms) and a duty cycle on the order of about 5% (resulting in an "on" period $T_2$ of 0.4 milliseconds and an "off" period of 7.6 milliseconds) were used. These results were obtained when the transducers were driven at 300 kHz to deliver 1 watt/transducer average power at the skin surface. During each "on" time $T_2$, therefore, approximately 120 cycles of ultrasound were delivered. The surprising results obtained at these rates lead us to conclude that the contribution of the ultrasound to the lysis of a thrombus is most, effective during the early portions of each activation, and that thus more frequent activation, but with significant rest intervals, is more effective in the lytic process. A typical course of treatment will take on the order of sixty minutes or so, and, for longer term therapy, may be repeated daily or even more often and over the course of days or weeks.

Uniformity of the field at the site of treatment is highly desirable. In accordance with the present invention, during the activation period of each transducer group, the transducers are driven alternately in-phase and out-of-phase. For example, as shown in FIG. 8A, during one segment of the period, e.g., segment (a), the transducers in the driven group are driven in-phase; during another segment, e.g., segment (b), they are driven out-of-phase. As illustrated, the duration of the in-phase and opposed-phase segments are preferably, though not necessarily, of equal duration.

FIG. 8B shows two alternative driving sequences that may usefully be used in connection with the present invention. The upper portion 100a of FIG. 8B shows a pairwise driving sequence, while the lower portion, 100b, shows a triplet driving sequence. In each of these, a plus sign ("+") indicates a first phase (e.g., 0 degrees); a minus sign ("−") indicates an opposite phase (e.g., 180 degrees); and the absence of an entry indicates that the transducer is not driven at a particular moment. Thus, a pairwise energization first energizes transducers 110 and 112 in the same phase, while transducer 114 remains inactive, i.e., unenergized (portion 100a, first line); then energizes transducers 110, 112 in opposite phase (second line); then energizes transducers 110 and 114 in the same phase, while transducer 112 is inactive (third line); etc. Since each transducer is inactive for one third of an operational cycle in pairwise energization, transducer heating is lower than it would be in continuous energization of the transducers throughout an operational cycle.

Portion 100b of FIG. 8B shows an alternative mode of energization cycle. In this mode, all the transducers of a group are energized at all times. In particular, a group of three transducers may begin an operational cycle with all transducers energized in the same phase (portion 100b, line 1). For the next portion of the energization cycle, the phase of one of the transducers (e.g., transducer 114) is inverted (indicated by the minus sign in line 2 of portion 100b); then transducers 110 and 114 are driven in phase while the phase of transducer 112 is inverted (line 3); etc.

It will be understood that additional transducers can be added to the array and operated in a similar manner to that described above. Further, it will be understood that while simple binary phase shifts of 0 and 180 degrees, respectively, produce useful results and have the benefit of simplicity in implementation, phase shifts of other magnitudes may advantageously be employed, e.g., 0, 120 and 240 degrees; 0, 90, 180, and 270 degrees; etc. Increasing the number of phases increases the smoothness of the resultant acoustic field, but also increases the complexity of the driving and control system.

Figure 9A:
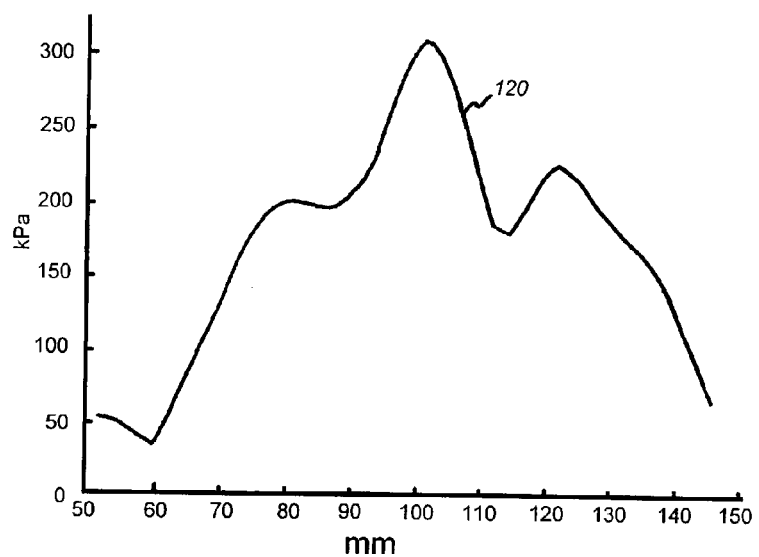
FIGS. 9A-9C are plots of the energy distribution within the skull provided by the array.
Figure 9B:
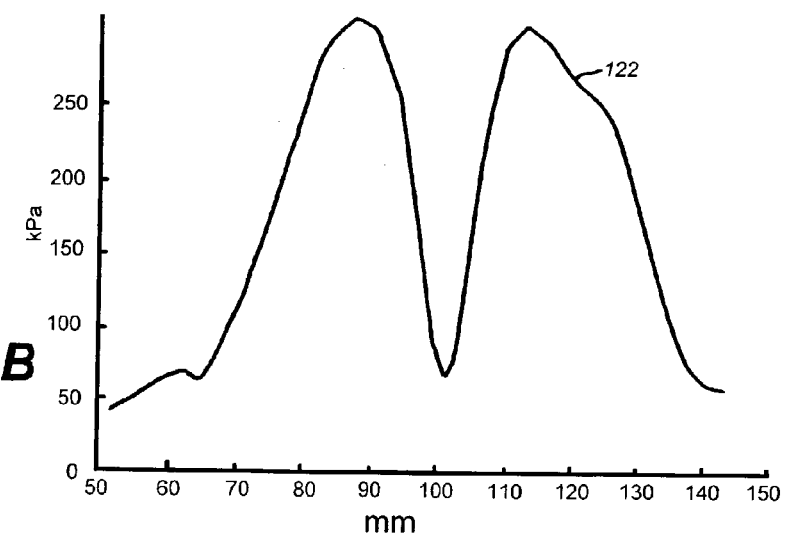
Figure 9C:
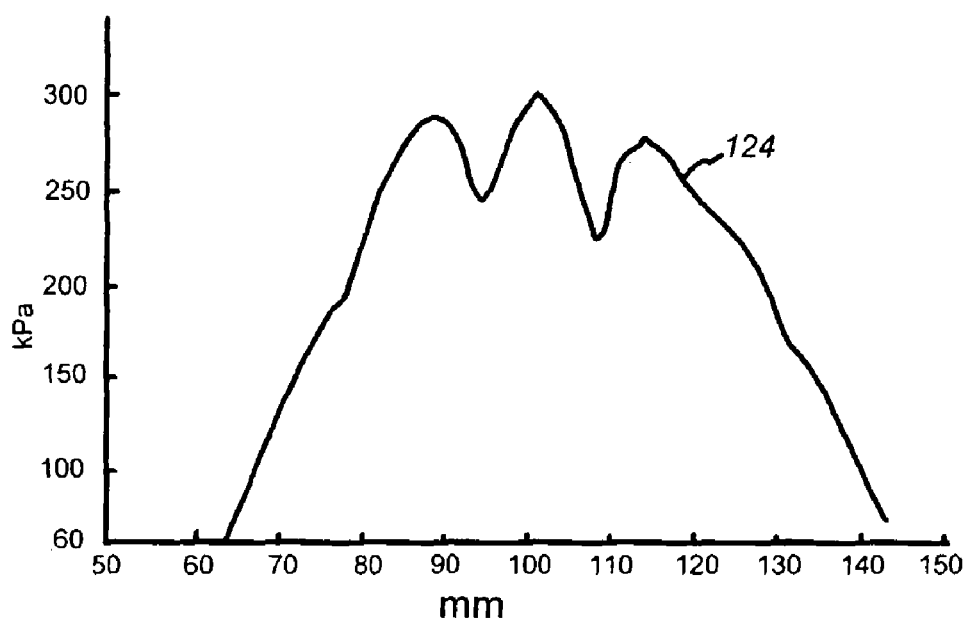

The effect of these approaches in smoothing out the average power delivered to the treatment site is illustrated in FIGS. 9A-9C which are plots of the signal intensity within a simulated test skull (in kiloPascals, kPa) against the lateral position relative to the beam center axis at 120 millimeters depth using pairwise transducer energization with alternating in-phase and opposed-phase energization. When the transducers are driven in-phase, the plot 120 of FIG. 9A is produced. When driven in opposed-phase (i.e., 180 degrees out of phase), the plot 122 of FIG. 9B is produced. Finally, when driven alternately in-phase and opposed-phase, plot 124 of FIG. 9C is produced. It will be seen that the resultant signal has a relatively flat amplitude (i.e., no greater than 3 db variation) over a distance of approximately 60 millimeters (6 cm) This is significantly greater than the 3 db beamwidth of an individual transducer, which is approximately only 1.2 cm. In contrast, a single transducer with a surface area equal to the total of the three transducers (e.g., 40 mm diameter) would have a −6 dB beam width of only 20 mm at 12 cm depth and would not provide the required field coverage. Further smoothing of the signal applied to the treatment region within the skull may be provided by cyclically varying the frequency of the driving signal to a given transducer by a small amount (e.g., +/−5 kHz).

Although we have focused so far on the application of our arrayed insonicator to the treatment of cranial thrombi and cerebral vascular insufficiency, we believe that it also has significant therapeutic effect on non-ischemic diseases such as Alzheimer's disease. In particular, it is known that medicaments such as statins appear to have neuroprotective properties arising from the stimulation of nitric oxide synthase systems, and it appears that administration of statins to those suffering from Alzheimer's disease ameliorates that disease. We believe that the stimulation of nitric oxide accompanying the insonication of a patient's brain in the manner described herein will lead to the same result and in a controlled manner. Because the energy intensity applied to the patient with the apparatus described herein is sufficiently low while nonetheless sufficient to meaningfully enhance collateral circulation, the insonication may be applied repeatedly over a is period of time without damage to the patient. For example, treatments of a duration of from 60 to 100 minutes each day over a period of several days to weeks can be expected to stop and even reverse neural damage from Alzheimer's disease.

From the foregoing, it will be seen that we have provided a significant tool, and method, for the treatment of cranial thrombi, cerebral vascular insufficiency, and other diseases or conditions. The tool takes the form of a transducer array mounted on a headpiece that is quickly and easily fitted to a patient, and thereafter activated, by attendants with even minimal training. It is wholly non-invasive, compact, and light weight, and well suited to use under emergency conditions such as in an ambulance or even in a stroke victim's home. The array provides a non-focused sonic field of significant intensity over a substantial region of the brain or other area at which it is directed. In preliminary testing of enhanced tPA thrombolysis, it has produced results that compare extremely favorably to catheter (intravenous or intra-arterial) insonication, yet the tool is wholly external and thus non-invasive.

It will be understood that various changes may be made in the above invention without departing from either the spirit or the scope thereof. For example, the headpiece may be structured to accommodate only a single transducer array. Conversely, two arrays may be used simultaneously to insonicate a region of the brain or other body part. Other changes may also be made and it should be understood that the foregoing is illustrative only, the scope of the invention being defined in the claims.

What is claimed is:

1. Apparatus for transcutaneous encephalic insonication, comprising an ultrasound transducer mounted on a support for positioning the transducer on the skull of a patient to be treated,
    said support having a receptacle for removably retaining a coolant pouch such that said coolant pouch contacts the skull of a patient to be treated when said support is fitted onto a patient, said support also having an inlet coolant tube retainer, and an outlet coolant tube retainer;
    a coolant pouch disposed in said receptacle, said coolant pouch providing acoustic coupling between said transducer and said skull, said coolant pouch having an inlet coolant tube retained in said inlet coolant tube retainer and an outlet coolant tube retained in said outlet coolant tube retainer;
    said transducer removably mounted on said support over said coolant pouch,
    said transducer comprising multiple transducer elements in which the energy beam from each transducer element has minimal overlap with the energy beam of each of the other transducer elements at the surface of the skull and having increasing overlap with the energy beam of at least one other transducer element within the skull, said transducer being energizable at one or more frequencies in the range of from 200 to 400 kHz for insonicating a region within the skull, wherein said transducer is energizable in a pulsed mode having an "on" time and an "off" time and the frequency at which said transducer is energized during said "on" time is varied while the transducer is energized over a range of frequencies within said range of from 200 to 400 kHz.

2. Apparatus according to claim 1 in which said transducer is energizable at frequencies in the vicinity of 300 kHz.

3. Apparatus according to claim 1 in which the frequency at which said transducer is energized is varied over a range of frequencies encompassing a central frequency.

4. Apparatus according to claim 3 in which the frequency at which said transducer is energized is varied over said range of frequencies in discrete steps.

5. Apparatus according to claim 3 in which the frequency at which said transducer is energized is varied over said range of frequencies in a generally continuous manner.

6. Apparatus according to claim 3 in which said central frequency is in the vicinity of 300 kHz.

7. Apparatus according to claim 3 in which the range of frequencies over which said transducer is energized is less than 10% of the central frequency.

8. Apparatus according to claim 3 in which the range of frequencies over which said transducer is energized is on the order of 3% of the central frequency.

9. Apparatus according to claim 1 in which said transducer comprises multiple transducer elements.

10. Apparatus according to claim 9 in which said multiple transducer elements comprise at least two elements concurrently energizable to insonicate said region.

11. Apparatus according to claim 10 in which said at least two elements are energizable in both in-phase and out-of-phase relationship with each other during a treatment interval.

12. Apparatus according to claim 10 in which said at least two elements are energizable in both in-phase and in opposed-phase relationship with each other during a treatment interval.

13. Apparatus according to claim 10 in which said elements are energized in a pulsed mode and in which the "on" time of at least one of said elements is less than its "off" time.

14. Apparatus according to claim 13 in which the "on" time of an element is no greater than 10% of the total "on" and "off" times.

15. Apparatus according to claim 14 in which the "on" time of an element is on the order of 5% of the "off" time.

16. Apparatus according to claim 10 in which said array comprises at least three transducer elements concurrently energizable in alternating pairs, each pair having respectively both in-phase and out-of-phase relationship with each other during a treatment interval.

17. Apparatus according to claim 10 in which said array comprises at least three transducer elements concurrently energizable, at least one of said elements having an out-of-phase relationship with another of said elements during at least part of a treatment interval.

18. Apparatus according to claim 17 in which said elements are arranged in a triangular pattern.

19. Apparatus according to claim 10 in which at least one of said transducer elements are driven out-of-phase with each other during said energization in order to provide a more nearly uniform field of insonication.

20. Apparatus according to claim 1 which includes a headband securable to the skull of said patient and having a frame thereon for receiving said transducer.

21. Apparatus according to claim 20 in which said frame carries a positioner for locating said frame in a defined relationship to one or more anatomical features of said skull.

22. Apparatus according to claim 21 in which said positioner is extendible into the meatus of the ear of the patient in order to define said relationship.

23. Apparatus according to claim 22 in which said positioner comprises a tapered insert for the ear.

24. Apparatus according to claim 23 in which said positioner comprises a plurality of resilient hemispherical elements aligned adjacent each other, said elements being of decreasing diameter with respect to each other and capable of generally conforming to the meatus for positioning said frame.

25. Apparatus according to claim 22 in which said positioner is rotatably mounted to said frame.

26. Apparatus according to claim 21 in which said positioner is located on said frame such that, when positioned in the meatus of the ear of a patient, it positions said frame over the temporal bone of the skull.

27. Apparatus according to claim 20 in which said headband comprises a plurality of straps adjustable to secure said frame to said skull.

28. Apparatus according to claim 20 in which said headband is mountable on said skull.

29. Apparatus according to claim 1 in which said pouch includes adapters thereon for releasably coupling said pouch to a source of coolant.

30. Apparatus according to claim 1 in which said pouch is formed of a flexible material conformable to both said skull and said transducer for providing acoustic coupling between said skull and said transducer.

31. Apparatus for treating a brain embolism or cerebral circulatory insufficiency, comprising an ultrasound transducer mounted on a support for positioning the transducer on the skull of a patient to be treated,
   said support having a receptacle for removably retaining a coolant pouch such that said coolant pouch contacts the skull of a patient to be treated when said support is fitted onto a patient, said support also having an inlet coolant tube retainer, and an outlet coolant tube retainer;
   a coolant pouch disposed in said receptacle, said coolant pouch providing acoustic coupling between said transducer and said skull, said coolant pouch having an inlet coolant tube retained in said inlet coolant tube retainer and an outlet coolant tube retained in said outlet coolant tube retainer;
   said transducer removably mounted on said support over said coolant pouch, said transducer comprising multiple transducer elements in which the energy beam from each transducer element has minimal overlap with the energy beam of each of the other transducer elements at the surface of the skull and having increasing overlap with the energy beam of at least one other transducer element within the skull, and a driver for applying an electrical driving signal to said transducer at one or more frequencies in the range of from 200 to 400 kHz for insonicating a region within the skull encompassing said embolism, wherein said driver and said transducer are configured to energize said transducer in a pulsed mode having an "on" time and an "off" time and the frequency at which said transducer is energized during said "on" time is varied while the transducer is energized over a range of frequencies within said range of from 200 to 400 kHz.

32. Apparatus according to claim 31 in which said transducer comprises a non-focusing group of elements, said driver being structured to energize at least some of said elements concurrently to thereby insonicate said region.

33. Apparatus according to claim 32 in which said driver is structured to drive at least some of said elements in out-of-phase relationship with each other during a treatment interval in order to provide a more nearly uniform field of insonication.

34. Apparatus according to claim 32 in which said driver is structured to energize at least some of said elements in opposed-phase relationship with each other during a treatment interval in order to provide a more nearly uniform field of insonication.

35. Apparatus according to claim 32 in which said driver is structured to energize said elements in a pulsed mode and in which the "on" time of an element is less than its "off" time.

36. Apparatus according to claim 32 in which said driver is structured to energize said elements in a pulsed mode and in which the "on" time of an element is on the order of 5% of its total "on" and "off" time.

37. Apparatus according to claim 32 in which said driver is structured to energize said elements at frequencies varying over a range of no more than 10% of a center frequency.

38. Apparatus according to claim 32 in which said multiple transducer elements comprise at least a set of three elements arranged in a triangular configuration.

39. Apparatus according to claim 32 which includes a headband securable to the skull of said patient and having a frame thereon for receiving said transducer.

40. Apparatus according to claim 32 in which said frame carries a positioner for locating said frame in a defined relationship to one or more anatomical features of said skull.

41. Apparatus according to claim 40 in which said positioner is extendible into the meatus of the ear of the patient in order to define said relationship.

42. Apparatus according to claim 41 in which said positioner comprises a tapered insert for the ear.

43. Apparatus according to claim 41 in which said positioner comprises a plurality of resilient hemispherical elements aligned adjacent each other, said elements being of decreasing diameter with respect to each other and capable of generally conforming to the meatus for positioning said frame.

44. Apparatus according to claim 43 in which said positioner is located on said frame such that, when positioned in the meatus of the ear of a patient, it positions said frame over the temporal bone of the skull.

45. Apparatus according to claim 31 in which said driver is structured to energize said transducer at frequencies in the vicinity of 300 kHz.

46. A method for insonicating a human brain within a skull for therapeutic treatment thereof, comprising:
   placing an inner headpiece onto the patient's head, said inner headpiece having a receptacle for removably retaining a coolant pouch such that said coolant pouch contacts the skull of a patient to be treated when said support is fitted onto a patient, said support also having an inlet coolant tube retainer, and an outlet coolant tube retainer;
   inserting a coolant pouch into said receptacle, said coolant pouch providing acoustic coupling between said transducer and said skull, and placing an inlet coolant tube into said inlet coolant tube retainer and an outlet coolant in said outlet coolant tube retainer;
   positioning an acoustic transducer over said coolant pouch, and
   acoustically insonicating said brain transcutaneously at one or more frequencies in the range of from 200 to 400 kHz, wherein said insonication is applied in a pulsed mode having an "on" time and an "off" time and the frequency of said insonication during said "on" time is varied while the transducer is energized over a range of frequencies within said range of from 200 to 400 kHz, wherein said insonication is produced by a transducer comprising multiple transducer elements in which the energy beam from each transducer element has minimal overlap with the energy beam of each of the other transducer elements at the surface of the skull and having increasing overlap with the energy beam of at least one other transducer element within the skull.

47. A method according to claim 46 in which said insonication is non-focused and is applied over a region of at least several centimeters in diameter.

48. A method according to claim 47 in which said insonication is applied from multiple acoustic radiating elements, at least some of which are driven our-of-phase with others of said elements in order to provide a more nearly uniform field over a region being treated.

49. A method according to claim 48 in which at least one of said elements are driven in opposed phase with respect to others of said elements in order to provide a more nearly uniform field over a region being treated.

50. A method according to claim 47 in which said insonication is applied from multiple acoustic radiating elements and in which said elements are driven in pulsed mode, the "on" time of said elements being substantially less than their "off" time.

51. A method according to claim 50 in which the "on" time of said elements is less than 10% of the total "on" and "off" times.

52. A method according to any of claims 46-51 for treatment of an embolism in the brain.

53. A method according to any of claims 46-51 for treatment of neuralgia.

54. A method according to any of claims 46-51 for increasing blood flow to regions of the brain by acoustically stimulating vasodilation.

55. A method according to any of claims 46-51 for increasing blood flow to regions of the brain by stimulating angiogenesis.

56. A method according to any of claims 46-51 for treating ischemic stroke.

57. A method according to any of claims 46-51 for treating Vascular Cognitive Impairment.

* * * * *